US006962645B2

(12) United States Patent
Graef et al.

(10) Patent No.: US 6,962,645 B2
(45) Date of Patent: Nov. 8, 2005

(54) RETICULATED ABSORBENT COMPOSITE

(75) Inventors: Peter A. Graef, Puyallup, WA (US); Fred B. Howard, Olalla, WA (US)

(73) Assignee: National Institute for Strategic Technology Acquisition, Manhattan, KS (US)

( * ) Notice: Subject to any disclaimer, the term of this patent is extended or adjusted under 35 U.S.C. 154(b) by 0 days.

(21) Appl. No.: 10/294,807

(22) Filed: Nov. 13, 2002

(65) Prior Publication Data

US 2003/0120236 A1 Jun. 26, 2003

Related U.S. Application Data

(62) Division of application No. 09/141,152, filed on Aug. 27, 1998, which is a continuation of application No. PCT/US98/09682, filed on May 12, 1998.
(60) Provisional application No. 60/046,395, filed on May 13, 1997.

(51) Int. Cl.[7] .......................... D21H 11/20; D21H 21/22
(52) U.S. Cl. .................... 162/100; 162/146; 162/157.6; 162/158; 162/164.1; 162/168.1; 162/183
(58) Field of Search ................................ 162/100, 101, 162/146, 157.6, 164.1, 168.1, 183, 158

(56) References Cited

U.S. PATENT DOCUMENTS

| | | |
|---|---|---|
| 3,716,449 A | 2/1973 | Gatward et al. |
| 3,871,952 A | 3/1975 | Robertson |
| 3,938,782 A | 2/1976 | Robertson |
| 4,354,901 A | 10/1982 | Kopolow |
| 4,364,992 A | 12/1982 | Ito et al. |
| 4,443,297 A | 4/1984 | Cheshire et al. |
| 4,551,142 A | 11/1985 | Kopolow |
| 4,559,050 A | 12/1985 | Iskra |
| 4,605,401 A | 8/1986 | Chmelir et al. |
| 4,798,603 A | 1/1989 | Meyer et al. |
| 4,885,204 A | 12/1989 | Bither et al. |
| 4,986,882 A | * 1/1991 | Mackey et al. ............. 162/109 |
| 4,988,344 A | 1/1991 | Reising et al. |
| 4,988,345 A | 1/1991 | Reising |
| 5,061,259 A | 10/1991 | Goldman et al. |
| 5,102,597 A | 4/1992 | Roe et al. |
| 5,134,007 A | 7/1992 | Reising et al. |
| 5,147,343 A | 9/1992 | Kellenberger |
| 5,147,345 A | 9/1992 | Young et al. |
| 5,149,335 A | 9/1992 | Kellenberger et al. |
| 5,200,036 A | * 4/1993 | Noda ..................... 162/164.3 |

(Continued)

FOREIGN PATENT DOCUMENTS

| | | |
|---|---|---|
| EP | 0 339 461 B1 | 11/1989 |
| EP | 437816 | * 7/1991 |
| EP | 0 437 816 B1 | 7/1995 |
| EP | 0 719 531 A1 | 3/1996 |
| EP | 0 724 870 A2 | 8/1996 |
| EP | 0 528 248 B1 | 10/1996 |
| FR | 2468689 | 5/1981 |
| GB | 2 060 018 A | 4/1981 |
| GB | 2 120 696 A | 12/1983 |
| GB | 2 254 255 A | 10/1992 |
| GB | 2 301 362 A | 12/1996 |
| WO | WO 97/05839 | 2/1997 |
| WO | WO 97/21453 | 6/1997 |
| WO | WO 98/24392 | 6/1998 |

*Primary Examiner*—Peter Chin
(74) *Attorney, Agent, or Firm*—Hovey Williams LLP

(57) ABSTRACT

An absorbent composite (10) having a fibrous matrix that includes absorbent material is disclosed. The fibrous matrix defines voids (14) and passages between the voids, which are distributed throughout the composite. Absorbent material (18) is located within some of the voids (14). Absorbent material located in these voids is expandable into the void. In a preferred embodiment, the composite's fibrous matrix includes resilient and matrix fibers (16). The composite optionally includes a wet strength agent.

16 Claims, 10 Drawing Sheets

U.S. PATENT DOCUMENTS

| | | | |
|---|---|---|---|
| 5,217,445 A | 6/1993 | Young et al. | |
| 5,277,915 A | 1/1994 | Provonchee et al. | |
| 5,281,207 A | 1/1994 | Chmielewski et al. | |
| 5,284,610 A | 2/1994 | Tai | |
| 5,324,561 A | 6/1994 | Rezai et al. | |
| 5,330,822 A | 7/1994 | Berg et al. | |
| 5,350,370 A | 9/1994 | Jackson et al. | |
| 5,354,290 A | 10/1994 | Gross | |
| 5,360,420 A | 11/1994 | Cook et al. | |
| 5,364,382 A | 11/1994 | Latimer et al. | |
| 5,372,877 A | 12/1994 | Kannankeril | |
| 5,415,643 A | 5/1995 | Kolb | |
| 5,422,169 A | 6/1995 | Roe | |
| 5,425,725 A | 6/1995 | Tanzer et al. | |
| 5,429,629 A | 7/1995 | Latimer et al. | |
| 5,486,167 A | 1/1996 | Dragoo et al. | |
| 5,505,718 A | 4/1996 | Roe et al. | |
| 5,522,810 A | 6/1996 | Allen, Jr. et al. | |
| 5,531,728 A | 7/1996 | Lash | |
| 5,562,646 A | 10/1996 | Goldman et al. | |
| 5,597,873 A | 1/1997 | Chambers et al. | |
| 5,599,335 A | 2/1997 | Goldman et al. | |
| 5,601,542 A | 2/1997 | Melius et al. | |
| 5,607,550 A * | 3/1997 | Akers | 162/102 |
| 5,637,105 A | 6/1997 | Tanaka et al. | |
| 5,651,862 A * | 7/1997 | Anderson et al. | 162/127 |
| 5,653,702 A | 8/1997 | Brohammer et al. | |
| 5,662,636 A * | 9/1997 | Benjamin et al. | 604/385.28 |
| 5,669,894 A | 9/1997 | Goldman et al. | |
| 5,698,078 A | 12/1997 | Mizukami et al. | |
| 5,795,439 A * | 8/1998 | Euripides et al. | 162/100 |
| 5,821,179 A | 10/1998 | Masaki et al. | |
| 5,830,202 A | 11/1998 | Bogdanski et al. | |
| 5,836,929 A | 11/1998 | Bewick-Sonntag et al. | |
| 5,843,059 A | 12/1998 | Niemeyer et al. | |
| 5,843,063 A | 12/1998 | Anderson et al. | |
| 5,843,575 A | 12/1998 | Wang et al. | |
| 5,843,852 A | 12/1998 | Dutkiewicz et al. | |
| 5,849,000 A | 12/1998 | Anjur et al. | |
| 5,849,405 A | 12/1998 | Wang et al. | |
| 5,851,672 A | 12/1998 | Wang et al. | |
| 5,853,867 A | 12/1998 | Harada et al. | |
| 5,855,572 A | 1/1999 | Schmidt | |
| 5,858,535 A | 1/1999 | Wang et al. | |
| 5,868,724 A | 2/1999 | Dierckes, Jr. et al. | |
| 5,873,867 A | 2/1999 | Coles et al. | |
| 5,891,120 A | 4/1999 | Chmielewski | |
| 5,941,862 A | 8/1999 | Haynes et al. | |
| 5,972,487 A | 10/1999 | Duenk et al. | |
| 5,977,014 A | 11/1999 | Plischke et al. | |
| 6,019,871 A * | 2/2000 | Rokman et al. | 162/101 |
| 6,020,536 A | 2/2000 | Österdahl et al. | |

* cited by examiner

RETICULATED ABSORBENT COMPOSITE

CROSS-REFERENCES TO RELATED APPLICATIONS

This application is a divisional of U.S. application Ser. No. 09/141,152, filed Aug. 27, 1998, which is a continuation of International application Ser. No. PCT/US98/09682, filed May 12, 1998, which claims the benefit of U.S. Provisional Application No. 60/046,395, filed May 13, 1997, priority of the filing dates of which is hereby claimed under 35 U.S.C. §§ 120 and 119, respectively. Each of these applications is incorporated herein by reference.

FIELD OF THE INVENTION

The present invention relates to an absorbent composite and more particularly, to a reticulated absorbent composite that includes superabsorbent material.

BACKGROUND OF THE INVENTION

Cellulose fibers derived from wood pulp are used in a variety of absorbent articles, for example, diapers, incontinence products, and feminine hygiene products. It is desirable for the absorbent articles to have a high absorbent capacity for liquid as well as to have good dry and wet strength characteristics for durability in use and effective fluid management. The absorbent capacity of articles made from cellulose fibers is often enhanced by the addition of superabsorbent materials, such as superabsorbent polymers. Superabsorbent polymers known in the art have the capability to absorb liquids in quantities from 5 to 100 times or more their weight. Thus, the presence of superabsorbent polymers greatly increases the liquid holding capacity of absorbent articles made from cellulose.

Because superabsorbent polymers absorb liquid and swell upon contact with liquid, superabsorbent polymers have heretofore been incorporated primarily in cellulose mats that are produced by the conventional dry, air-laid methods. Wet-laid processes for forming cellulose mats have not been used commercially because superabsorbent polymers tend to absorb liquid and swell during formation of the absorbent mats, thus requiring significant energy for their complete drying.

Cellulose structures formed by the wet-laid process typically exhibit certain properties that are superior to those of an air-laid structure. The integrity, fluid distribution, and the wicking characteristics of wet-laid cellulosic structures are superior to those of air-laid structures. Attempts to combine the advantages of wet-laid composites with the high absorbent capacity of superabsorbent materials has led to the formation of various wet-laid absorbent composites that include superabsorbent materials. Generally, these structures include superabsorbent materials distributed as a layer within a multilayered composite. Because the superabsorbent polymer is relatively localized and not uniformly distributed throughout the absorbent structure and thus renders these composites susceptible to gel blocking. Upon liquid absorption, superabsorbent materials tend to coalesce and form a gelatinous mass that prevents the wicking of liquid to unwetted portions of the composite. By preventing distribution of acquired liquid from a composite's unwetted portions, gel blocking precludes the effective and efficient use of superabsorbent materials in fibrous composites. The diminished capacity of such fibrous composites results from narrowing of capillary acquisition and distribution channels that accompanies superabsorbent material swelling. The diminution of absorbent capacity and concomitant loss of capillary distribution channels for conventional absorbent cores that include superabsorbent material are manifested by decreased liquid acquisition rates and far from ideal liquid distribution on successive liquid insults.

Accordingly, there exists a need for an absorbent composite that includes superabsorbent material and that effectively acquires and wicks liquid throughout the composite and distributes the acquired liquid to absorbent material where the liquid is efficiently absorbed and retained without gel blocking. A need also exists for an absorbent composite that continues to acquire and distribute liquid throughout the composite on successive liquid insults. In addition, there exists a need for an absorbent composition containing superabsorbent materials that exhibits the advantages associated with wet-laid composites including wet strength, absorbent capacity and acquisition, liquid distribution, softness, and resilience. The present invention seeks to fulfill these needs and provides further related advantages.

SUMMARY OF THE INVENTION

The present invention relates generally to a reticulated fibrous absorbent composite containing absorbent material and methods for its formation. The absorbent composite is a fibrous matrix that includes absorbent material and has a three-dimensional network of channels or capillaries. The composite's reticulated nature enhances liquid wicking, acquisition, and distribution, while the absorbent material provides high absorbent capacity. Wet strength agents can be incorporated into the composite to provide wet integrity and also assist in securing the absorbent material in the composite.

The absorbent composite includes a stable three-dimensional network of fibers and channels that afford rapid wicking and acquisition of liquid. The fibers and channels distribute the acquired liquid throughout the composite and direct liquid to absorbent material present in the composite where the liquid is ultimately absorbed. The composite maintains its integrity before, during, and after liquid is introduced. In one embodiment, the composite is a densified composite that can recover its original volume on wetting.

In one aspect, the present invention provides an absorbent composite having a fibrous matrix that includes absorbent material. The fibrous matrix defines voids and passages between the voids, which are distributed throughout the composite. Absorbent material is located within some of the voids. The absorbent material located in these voids is expandable into the void.

In another aspect of the present invention, methods for forming a reticulated absorbent composite are provided. In the methods, the absorbent composite is formed from a wet composite that incorporates absorbent material. The method generally includes forming a wet composite from a mixture of fibers, absorbent material and, optionally, a wet strength agent in a dispersion medium, and then drying the wet composite to provide the composite of the present invention. In one embodiment of the method, the absorbent material hydrates and swells when combined with the dispersion medium in the slurry. Drying the wet composite results in dehydration of the swollen absorbent material accompanied by decrease in the absorbent material's size. The decrease in size of the swollen absorbent material results in the formation of voids in the dried absorbent composite. The voids are connected by a network of fibers and channels that provide for liquid acquisition, distribution, and absorption. In one embodiment of the method, the composite is formed by a wet-laid method and, in another embodiment, the composite is formed by a foam method.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

Figure 1:
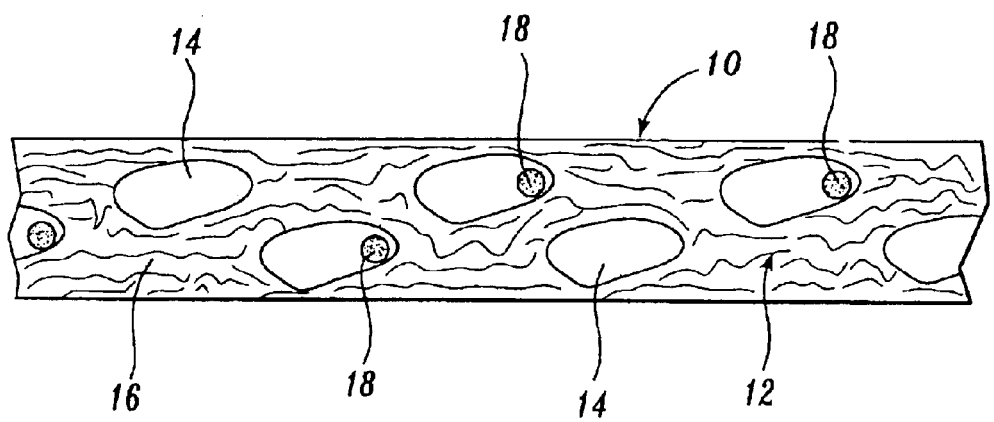
FIG. 1 is a cross-sectional view of a portion of a reticulated absorbent composite formed in accordance with the present invention.

The absorbent composite of the present invention is a reticulated fibrous composite that includes absorbent material. The absorbent material is distributed substantially throughout the fibrous composite and serves to absorb and retain liquid acquired by the composite. In a preferred embodiment, the absorbent material is a superabsorbent material. In addition to forming a matrix for the absorbent material, the composite's fibers provide a stable three-dimensional network of channels or capillaries that serve to acquire liquid contacting the composite and to distribute the acquired liquid to the absorbent material. The composite of the present invention optionally includes a wet strength agent that further increases tensile strength and structural integrity of the composite.

The present composite is a fibrous matrix that includes absorbent material. The fibrous matrix defines voids and passages between the voids, which are distributed throughout the composite. Absorbent material is located within some of the voids. The absorbent material located in these voids is expandable into the void.

The absorbent composite can be advantageously incorporated into a variety of absorbent articles such as diapers and training pants; feminine care products including sanitary napkins, tampons, and pant liners; adult incontinence products; toweling; surgical and dental sponges; bandages; food tray pads; and the like.

Because the composite is highly absorbent having a high liquid storage capacity, the composite can be incorporated into an absorbent article as a liquid storage core. In such a construct, the composite can be combined with one or more other composites or layers including, for example, an acquisition and/or distribution layer. In one preferred embodiment, the present invention provides an absorbent article, such as a diaper, that includes an acquisition layer overlying a reticulated storage core and having a liquid pervious facing sheet and a liquid impervious backing sheet. Because of the composite's capacity to rapidly acquire and distribute liquid, the composite can serve as a liquid management layer that acquires and transfers a portion of the acquired liquid to an underlying storage layer. Thus, in another embodiment, the absorbent composite can be combined with a storage layer to provide an absorbent core that is useful in absorbent articles.

The absorbent composite of the present invention is a reticulated absorbent composite. As used herein, the term "reticulated" refers to the composite's open and porous nature characterized as having a stable three-dimensional network of fibers (i.e., fibrous matrix) that create channels or capillaries that serve to rapidly acquire and distribute liquid throughout the composite, ultimately delivering acquired liquid to the absorbent material that is distributed throughout the composite.

The reticulated composite of the present invention is an open and stable structure. The fibrous composite's open and stable structure includes a network of capillaries or channels that are effective in acquiring and distributing liquid throughout the composite. In the composite, fibers form relatively dense bundles that direct fluid throughout the composite and to absorbent material distributed throughout the composite. The composite's wet strength agent serves to stabilize the fibrous structure by providing interfiber bonding. The interfiber bonding assists in providing a composite having a stable structure in which the composite's capillaries or channels remain open before, during, and after liquid insult. The composite's stable structure provides capillaries that remain open after initial liquid insult and that are available for acquiring and distributing liquid on subsequent insults.

Referring to FIG. 1, a representative reticulated absorbent composite, indicated generally by reference numeral 10, formed in accordance with the present invention is a fibrous matrix that includes fibrous regions 12 substantially composed of fibers 16 and defining voids 14. Some voids include absorbent material 18. Voids 14 are distributed throughout composite 10.

Figure 2:
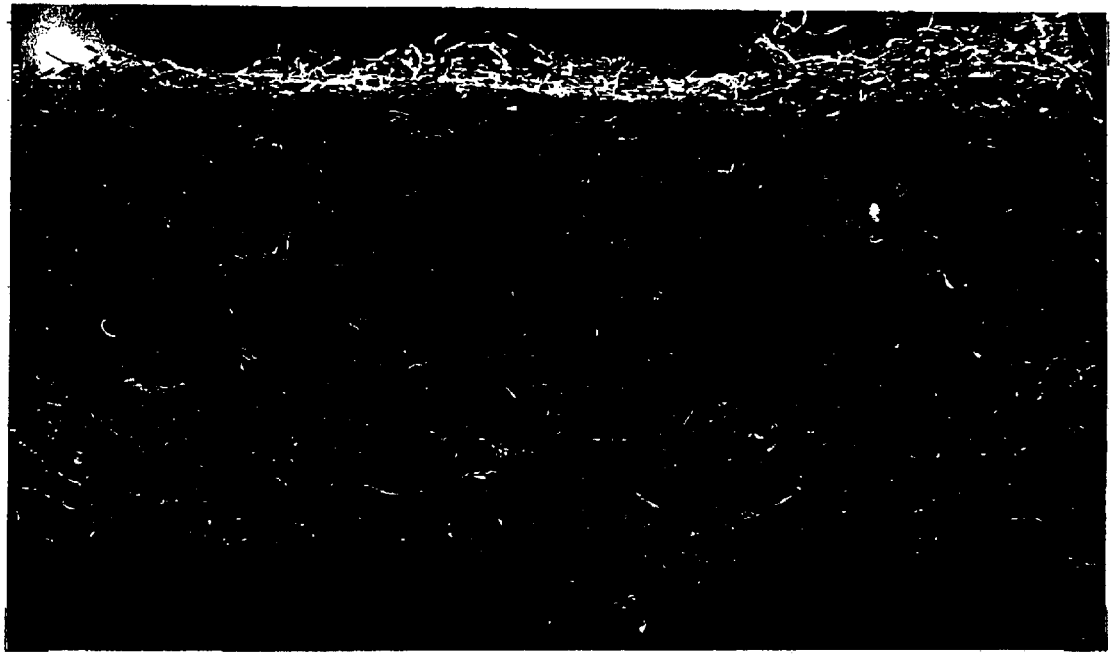
FIG. 2 is a photomicrograph of a cross section of a representative reticulated absorbent composite formed by a wet-laid method in accordance with the present invention at 12 times magnification.
Figure 3:
FIG. 3 is a photomicrograph of the wet-laid composite of FIG. 2 at 40 times magnification.
Figure 4:
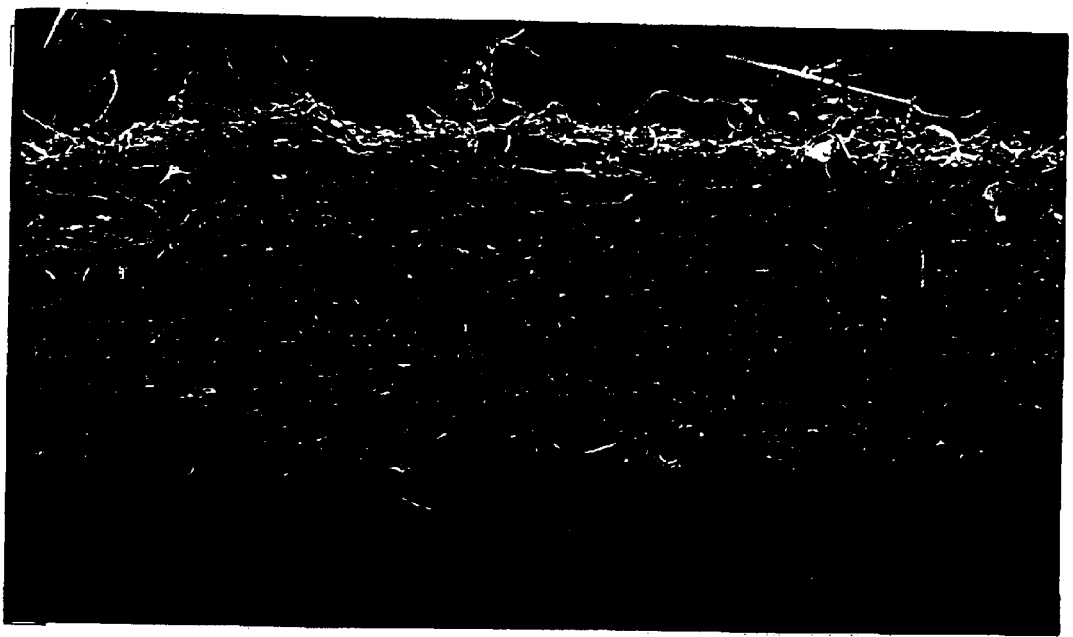
FIG. 4 is a photomicrograph of a cross section of a representative reticulated absorbent composite formed by a foam method in accordance with the present invention at 12 times magnification.
Figure 5:
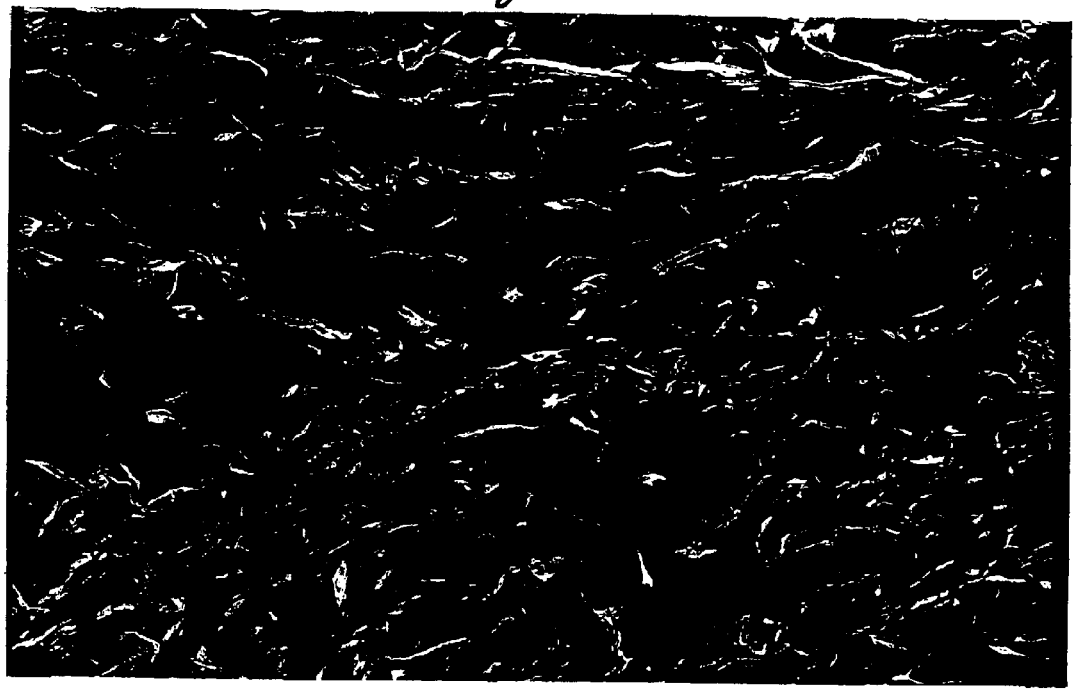
FIG. 5 is a photomicrograph of the foam-formed composite of FIG. 4 at 40 times magnification.

Representative reticulated composites of the invention are shown in FIGS. 2–9. These composites include 48 percent by weight matrix fibers (i.e., southern pine commercially available from Weyerhaeuser Co. under the designation NB416), 12 percent by weight resilient fibers (i.e., polymaleic acid crosslinked fibers), 40 percent by weight absorbent material (i.e., superabsorbent material commercially available from Stockhausen), and about 0.5 percent by weight wet strength agent (i.e., polyamide-epichlorohydrin resin commercially available from Hercules under the designation Kymene®). FIG. 2 is a photomicrograph of a cross section of a representative composite of the invention formed by a wet-laid process at 12 times magnification. FIG. 3 is a photomicrograph of the same cross section at 40 times magnification. FIG. 4 is a photomicrograph of a cross section of a representative composite of the invention formed by a foam process at 12 times magnification. FIG. 5 is a photomicrograph of the same cross section at 40 times magnification. The reticulated nature of the composites is shown in these figures. Referring to FIG. 3, fibrous regions extend throughout the composite, creating a network of channels. Void regions, including those that include absorbent material, appear throughout the composite and are in fluid communication with the composite's fibrous regions. Absorbent material appears in the composite's voids, generally surrounded by dense fiber bundles.

Figure 6:
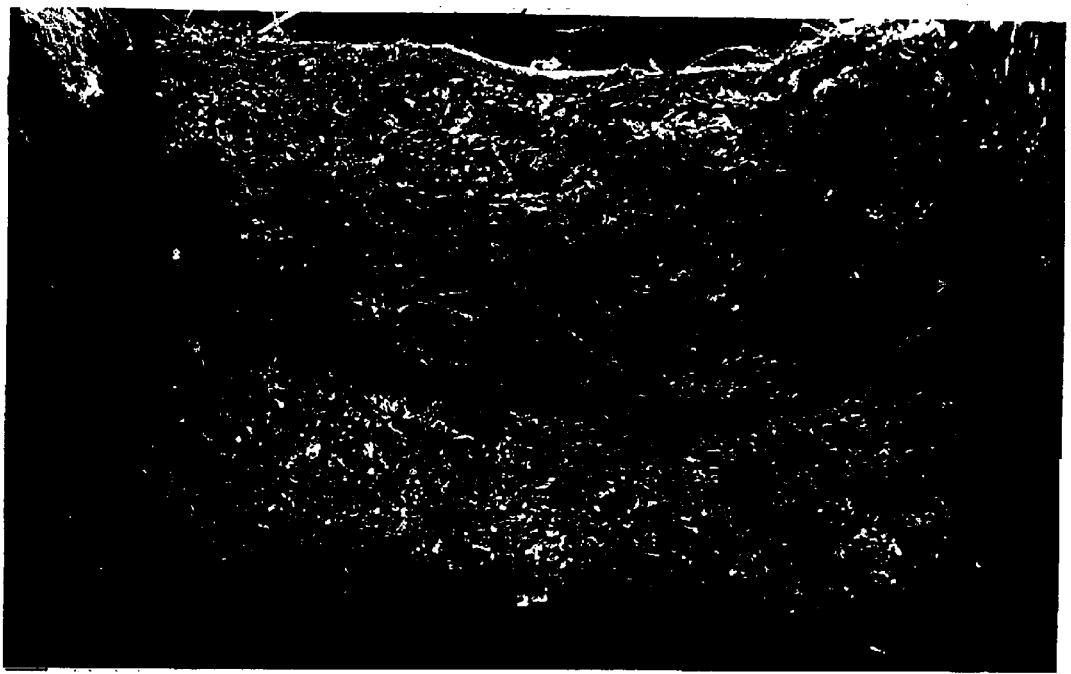
FIG. 6 is a photomicrograph of a cross section of a representative reticulated absorbent composite formed by a wet-laid method in accordance with the present invention in a wetted state at 8 times magnification.
Figure 7:
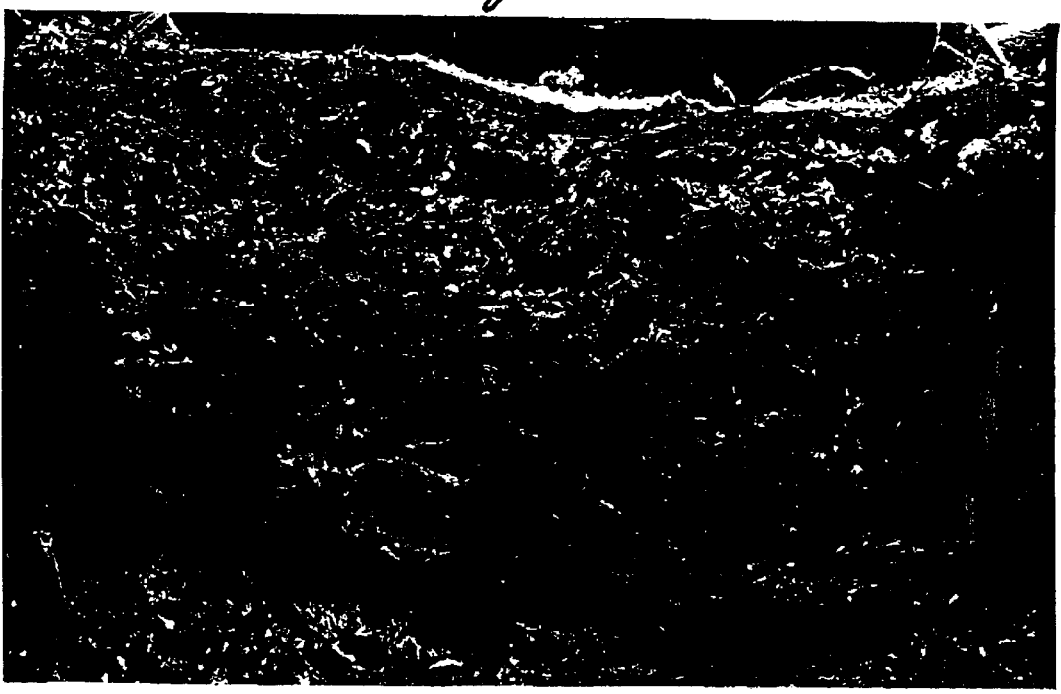
FIG. 7 is a photomicrograph of the wet-laid composite of FIG. 6 at 12 times magnification.
Figure 8:
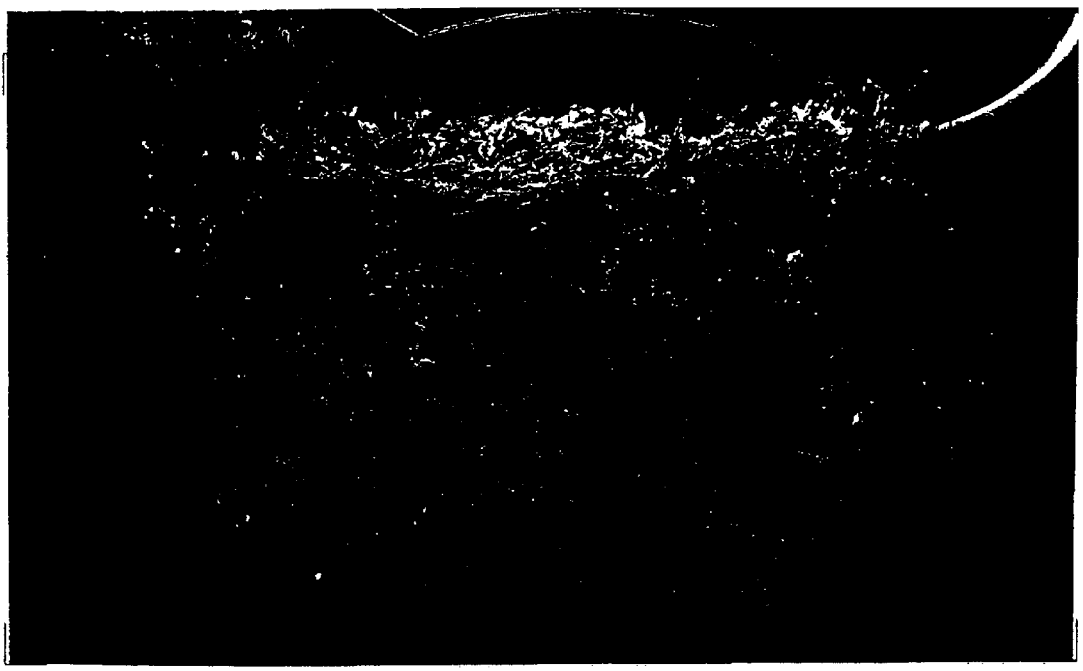
FIG. 8 is a photomicrograph of a cross section of a representative reticulated absorbent composite formed by a foam method in accordance with the present invention in a wetted state at 8 times magnification.
Figure 9:
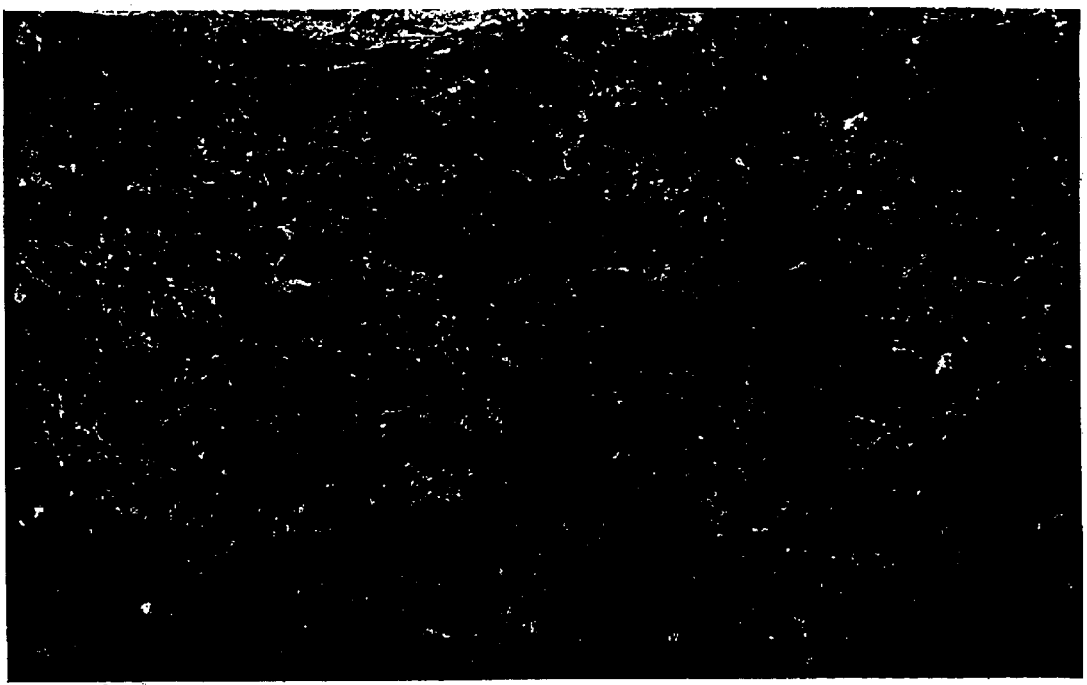
FIG. 9 is a photomicrograph of the foam-formed composite of FIG. 8 at 12 times magnification.

Photomicrographs of the representative composites shown in FIGS. 2–5 in a wetted state are illustrated in FIGS. 6–9, respectively. These photomicrographs were obtained by sectioning freeze-dried composites that had acquired synthetic urine under free swell conditions. FIGS. 6 and 7 are photomicrographs of the wetted wet-laid composite at 8 times and 12 times magnification, respectively. FIGS. 8 and 9 are photomicrographs of the wetted foam-formed composite at 8 times and 12 times magnification, respectively. Referring to FIG. 6, absorbent material in the wetted composite has swollen and increased in size to more fully occupy voids that the absorbent material previously occupied in the dry composite.

The composite's fibrous matrix is composed primarily of fibers. Generally, fibers are present in the composite in an amount from about 20 to about 90 weight percent, preferably from about 50 to about 70 weight percent, based on the total weight of the composite. Fibers suitable for use in the present invention are known to those skilled in the art and include any fiber from which a wet composite can be formed.

The composite of the invention includes resilient fibers. As used herein, the term "resilient fiber" refers to a fiber present in the composite that imparts reticulation to the composite. Generally, resilient fibers provide the composite with bulk and resiliency. The incorporation of resilient fibers into the composite allows the composite to expand on absorption of liquid without structural integrity loss. Resilient fibers also impart softness to the composite. In addition, resilient fibers offer advantages in the composite's formation processes. Because of the porous and open structure resulting from wet composites that include resilient fibers, these composites drain water relatively easily and are therefore dewatered and dried more readily than wet composites that do not include resilient fibers. Preferably, the composite includes resilient fibers in an amount from about 5 to about 60 percent by weight, more preferably from about 10 to 40 percent by weight, based on the total weight of the composite.

Resilient fibers include cellulosic and synthetic fibers. Preferred resilient fibers include chemically stiffened fibers, anfractuous fibers, chemithermomechanical pulp (CTMP), and prehydrolyzed kraft pulp (PHKP).

The term "chemically stiffened fiber" refers to a fiber that has been stiffened by chemical means to increase fiber stiffness under dry and wet conditions. Fibers can be stiffened by the addition of chemical stiffening agents that can coat and/or impregnate the fibers. Stiffening agents include the polymeric wet strength agents including resinous agents such as, for example, polyamide-epichlorohydrin and polyacrylamide resins described below. Fibers can also be stiffened by modifying fiber structure by, for example, chemical crosslinking. Preferably, the chemically stiffened fibers are intrafiber crosslinked cellulosic fibers.

Resilient fibers can include noncellulosic fibers including, for example, synthetic fibers such as polyolefin, polyamide, and polyester fibers. In a preferred embodiment, the resilient fibers include crosslinked cellulosic fibers.

As used herein, the term "anfractuous fiber" refers to a cellulosic fiber that has been chemically treated. Anfractuous fibers include, for example, fibers that have been treated with ammonia.

In addition to resilient fibers, the composite of the invention includes matrix fibers. As used herein, the term "matrix fiber" refers to a fiber that is capable of forming hydrogen bonds with other fibers. Matrix fibers are included in the composite to impart strength to the composite. Matrix fibers include cellulosic fibers such as wood pulp fibers, highly refined cellulosic fibers, and high surface area fibers such as expanded cellulose fibers. Other suitable cellulosic fibers include cotton linters, cotton fibers, and hemp fibers, among others. Mixtures of fibers can also be used. Preferably, the composite includes matrix fibers in an amount from about 10 to about 60 percent by weight and more preferably from about 20 to about 50 percent by weight, based on the total weight of the composite.

The composite of the present invention preferably includes a combination of resilient and matrix fibers. In one preferred embodiment, the composite includes resilient fibers in an amount from about 5 to about 20 percent by weight and matrix fibers in an amount from about 20 to about 60 percent by weight, based on the total weight of the composite. In a more preferred embodiment, the composite includes from about 10 to about 15 percent by weight resilient fibers, preferably crosslinked cellulosic fibers, and from about 40 to about 50 percent by weight matrix fibers, preferably wood pulp fibers, based on the total weight of the composite.

Cellulosic fibers are a basic component of the absorbent composite of the present invention. Although available from other sources, cellulosic fibers are derived primarily from wood pulp. Suitable wood pulp fibers for use with the invention can be obtained from well-known chemical processes such as the kraft and sulfite processes, with or without subsequent bleaching. The pulp fibers may also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. Softwoods and hardwoods can be used. Details of the selection of wood pulp fibers are well known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, PL416, FR516, and NB416.

The wood pulp fibers of the present invention can also be pretreated prior to use with the present invention. This pretreatment may include physical treatment, such as subjecting the fibers to steam, or chemical treatment, for example, crosslinking the cellulose fibers using any one of a variety of crosslinking agents. Crosslinking increases fiber bulk and resiliency, and thereby can improve the fibers' absorbency. Generally, crosslinked fibers are twisted or crimped. The use of crosslinked fibers allows the composite to be more resilient, softer, bulkier, have better wicking, and be easier to densify than a composite that does not include crosslinked fibers. Suitable crosslinked cellulose fibers produced from southern pine are available from Weyerhaeuser Company under the designation NHB416. Crosslinked cellulose fibers and methods for their preparation are disclosed in U.S. Pat. Nos. 5,437,418 and 5,225,047 issued to Graef et al., expressly incorporated herein by reference.

Intrafiber crosslinked cellulosic fibers are prepared by treating cellulose fibers with a crosslinking agent. Suitable cellulose crosslinking agents include aldehyde and urea-based formaldehyde addition products. See, for example, U.S. Pat. Nos. 3,224,926; 3,241,533; 3,932,209; 4,035,147; 3,756,913; 4,689,118; 4,822,453; U.S. Pat. No. 3,440,135, issued to Chung; U.S. Pat. No. 4,935,022, issued to Lash et al.; U.S. Pat. No. 4,889,595, issued to Herron et al.; U.S. Pat. No. 3,819,470, issued to Shaw et al.; U.S. Pat. No. 3,658,613, issued to Steijer et al.; and U.S. Pat. No. 4,853,086, issued to Graef et al., all of which are expressly incorporated herein by reference in their entirety. Cellulose fibers have also been crosslinked by carboxylic acid crosslinking agents including polycarboxylic acids. U.S. Pat. Nos. 5,137,537; 5,183,707; and 5,190,563, describe the use of $C_2$–$C_9$ polycarboxylic acids that contain at least three carboxyl groups (e.g., citric acid and oxydisuccinic acid) as crosslinking agents.

Suitable urea-based crosslinking agents include methylolated ureas, methylolated cyclic ureas, methylolated lower alkyl cyclic ureas, methylolated dihydroxy cyclic ureas, dihydroxy cyclic ureas, and lower alkyl substituted cyclic ureas. Specific preferred urea-based crosslinking agents include dimethyldihydroxy urea (DMDHU, 1,3-dimethyl-4,5-dihydroxy-2-imidazolidinone), dimethyloldihydroxyethylene urea (DMDHEU, 1,3-dihydroxymethyl-4,5-dihydroxy-2-imidazolidinone), dimethylol urea (DMU, bis[N-hydroxymethyl]urea), dihydroxyethylene urea (DHEU, 4,5-dihydroxy-2-imidazolidinone), dimethylolethylene urea (DMEU, 1,3-dihydroxymethyl-2-imidazolidinone), and dimethyl-dihydroxyethylene urea (DDI, 4,5-dihydroxy-1,3-dimethyl-2-imidazolidinone).

Suitable polycarboxylic acid crosslinking agents include citric acid, tartaric acid, malic acid, succinic acid, glutaric acid, citraconic acid, itaconic acid, tartrate monosuccinic acid, and maleic acid. Other polycarboxylic acids crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. patent application Ser. No. 08/989,697, filed Dec. 12, 1997, and assigned to Weyerhaeuser Company. Mixtures or blends of crosslinking agents can also be used.

The crosslinking agent can include a catalyst to accelerate the bonding reaction between the crosslinking agent and cellulose fiber. Suitable catalysts include acidic salts, such as ammonium chloride, ammonium sulfate, aluminum chloride, magnesium chloride, and alkali metal salts of phosphorous-containing acids.

Although not to be construed as a limitation, examples of pretreating fibers include the application of surfactants or other liquids that modify the surface chemistry of the fibers. Other pretreatments include incorporation of antimicrobials, pigments, dyes and densification or softening agents. Fibers pretreated with other chemicals, such as thermoplastic and thermosetting resins also may be used. Combinations of pretreatments also may be employed. Similar treatments can also be applied after the composite formation in post-treatment processes.

Cellulosic fibers treated with particle binders and/or densification/softness aids known in the art can also be employed in accordance with the present invention. The particle binders serve to attach other materials, such as cellulosic fiber superabsorbent polymers, as well as others, to the cellulosic fibers. Cellulosic fibers treated with suitable particle binders and/or densification/softness aids and the process for combining them with cellulose fibers are disclosed in the following U.S. patents and patent applications: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet-laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Pat. No. 5,308,896, entitled "Particle Binders for High-Bulk Fibers"; (6) Ser. No. 07/931,279, filed Aug. 17, 1992, entitled "Particle Binders that Enhance Fiber Densification"; (7) Ser. No. 08/107,469, filed Aug. 17, 1993, entitled "Particle Binders"; (8) Ser. No. 08/107,219, filed Aug. 17, 1993, entitled "Particle Binding to Fibers"; (9) Ser. No. 08/107,467, filed Aug. 17, 1993, entitled "Binders for Binding Water Soluble Particles to Fibers"; (10) U.S. Pat. No. 5,547,745, entitled "Particle Binders"; (11) Ser. No. 08/108,218, filed Aug. 17, 1993, entitled "Particle Binding to Fibers" and (12) U.S. Pat. No. 5,308,896, entitled "Particle Binders for High-Bulk Fibers"; all expressly incorporated herein by reference.

In addition to natural fibers, synthetic fibers including polymeric fibers, such as polyolefin, polyamide, polyester, polyvinyl alcohol, and polyvinyl acetate fibers may also be used in the absorbent composite of the present invention. Suitable polyolefin fibers include polyethylene and polypropylene fibers. Suitable polyester fibers include polyethylene terephthalate fibers. Other suitable synthetic fibers include, for example, nylon fibers. The absorbent composite can include combinations of natural and synthetic fibers.

In one preferred embodiment, the absorbent composite includes a combination of wood pulp fibers (e.g., Weyerhaeuser designation NB416) and crosslinked cellulosic fibers (e.g., Weyerhaeuser designation NHB416). Wood pulp fibers are present in such a combination in an amount from about 10 to about 85 weight percent by weight based on the total weight of fibers.

When incorporated into an absorbent article, the reticulated absorbent composite of the present invention can serve as a storage layer for acquired liquids. To effectively retain acquired liquids, the absorbent composite includes absorbent material. As used herein, the term "absorbent material" refers to a material that absorbs liquid and that generally has an absorbent capacity greater than the cellulosic fibrous component of the composite. Preferably, the absorbent material is a water-swellable, generally water-insoluble polymeric material capable of absorbing at least about 5, desirably about 20, and preferably about 100 or more times its weight in saline (e.g., 0.9 percent saline). The absorbent material can be swellable in the dispersion medium utilized in the method for forming the composite. In one embodiment, the absorbent material is untreated and swellable in the dispersion medium. In another embodiment, the absorbent material is a coated absorbent material that is resistant to absorbing water during the composite formation process.

The amount of absorbent material present in the composite can vary greatly depending on the composite's intended use. The amount of absorbent material present in an absorbent article, such as an absorbent core for an infant's diaper, is suitably present in the composite in an amount from about 5 to about 60 weight percent, preferably from about 30 to about 50 weight percent, based on the total weight of the composite.

The absorbent material may include natural materials such as agar, pectin, and guar gum, and synthetic materials, such as synthetic hydrogel polymers. Synthetic hydrogel polymers include, for example, carboxymethyl cellulose, alkaline metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulphonic acid, polyacrylates, polyacrylamides, and polyvinyl pyridine among others. In a preferred embodiment, the absorbent material is a superabsorbent material. As used herein, a "superabsorbent material" refers to a polymeric material that is capable of absorbing large quantities of fluid by swelling and forming a hydrated gel (i.e., a hydrogel). In addition to absorbing large quantities of fluids, superabsorbent materials can also retain significant amounts of bodily fluids under moderate pressure.

Superabsorbent materials generally fall into three classes: starch graft copolymers, crosslinked carboxymethylcellulose derivatives, and modified hydrophilic polyacrylates. Examples of such absorbent polymers include hydrolyzed starch-acrylonitrile graft copolymers, neutralized starch-acrylic acid graft copolymers, saponified acrylic acid ester-vinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

Superabsorbent materials are available commercially, for example, polyacrylates from Clariant of Portsmouth, Va. These superabsorbent polymers come in a variety of sizes, morphologies, and absorbent properties (available from Clariant under trade designations such as IM 3500 and IM 3900). Other superabsorbent materials are marketed under the trademarks SANWET (supplied by Sanyo Kasei Kogyo Kabushiki Kaisha), and SXM477 (supplied by Stockhausen of Greensboro, N.C.). Other superabsorbent materials are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598, all expressly incorporated herein by reference. Products such as diapers that incorporate superabsorbent materials are described in U.S. Pat. No. 3,699,103 and U.S. Pat. No. 3,670,731.

Suitable superabsorbent materials useful in the absorbent composite of the present invention include superabsorbent particles and superabsorbent fibers.

In a preferred embodiment, the absorbent composite of the present invention includes a superabsorbent material that swells relatively slowly for the purposes of composite manufacturing and yet swells at an acceptable rate so as not to adversely affect the absorbent characteristics of the composite or any construct containing the composite. Generally, the smaller the absorbent material, the more rapidly the material absorbs liquid.

The absorbent composite of this invention can optionally include a wet strength agent. The wet strength agent provides increased strength to the absorbent composite and enhances the composite's wet integrity. In addition to increasing the composite's wet strength, the wet strength agent can assist in binding the absorbent material, for example, superabsorbent material, in the composite's fibrous matrix.

Suitable wet strength agents include cationic modified starch having nitrogen-containing groups (e.g., amino groups) such as those available from National Starch and Chemical Corp., Bridgewater, N.J.; latex; wet strength resins such as polyamide-epichlorohydrin resin (e.g., Kymene® 557LX, Hercules, Inc., Wilmington, Del.), polyacrylamide resin (described, for example, in U.S. Pat. No. 3,556,932 issued Jan. 19, 1971 to Coscia et al.; also, for example, the commercially available polyacrylamide marketed by American Cyanamid Co., Stanford, Conn., under the trade name Parez™ 631 NC); urea formaldehyde and melamine formaldehyde resins, and polyethylenimine resins. A general discussion on wet strength resins utilized in the paper field, and generally applicable in the present invention, can be found in TAPPI monograph series No. 29, "Wet Strength in Paper and Paperboard", Technical Association of the Pulp and Paper Industry (New York, 1965).

Generally, the wet strength agent is present in the composition in an amount from about 0.01 to about 2 weight percent, preferably from about 0.1 to about 1 weight percent, and more preferably from about 0.3 to about 0.7 weight percent, based on the total weight of the composite. In a preferred embodiment, the wet strength agent useful in forming the composite of the present invention is a polyamide-epichlorohydrin resin commercially available from Hercules, Inc. under the designation Kymene®. The wet and dry tensile strength of an absorbent composite formed in accordance with the present invention will generally increase with increasing the amount of wet strength agent. The tensile strength of a representative composite of this invention is described in Example 7.

The absorbent composite of the present invention generally has a basis weight from about 50 to about 1000 g/m², preferably from about 200 to about 800 g/m². In a more preferred embodiment, the absorbent composite has a basis weight from about 300 to about 600 g/m². The absorbent composite generally has a density from about 0.02 to about 0.7 g/cm³, preferably from about 0.04 to about 0.3 g/cm³. In a more preferred embodiment, the absorbent composite has a density of about 0.15 g/cm³.

In one embodiment, the absorbent composite is a densified composite. Densification methods useful in producing the densified composites of the present invention are well known to those in the art. See, for example, U.S. Pat. No. 5,547,541 and patent application Ser. No. 08/859,743, filed May 21, 1997, entitled "Softened Fibers and Methods of Softening Fibers," assigned to Weyerhaeuser Company, both expressly incorporated herein by reference. Postdryer densified absorbent reticulated storage composites of this invention generally have a density from about 0.1 to about 0.5 g/cm³, and preferably about 0.15 g/cm³. Predryer densification can also be employed. Preferably, the absorbent composite is densified by either a heated or room temperature calender roll method. See, for example, U.S. Pat. Nos. 5,252,275 and 5,324,575, both expressly incorporated herein by reference.

The composition of the reticulated absorbent composite of the present invention can be varied to suit the needs of the desired end product in which it is incorporated. In one preferred embodiment, the absorbent composite of the present invention includes about 60 weight percent cellulosic fibers (about 48 percent by weight wood pulp fibers and about 12 percent by weight crosslinked cellulosic fibers), about 40 percent by weight absorbent material (e.g., superabsorbent particles), and about 0.5 percent by weight wet strength agent (e.g., polyamide-epichlorohydrin resin, Kymene®, about 10 pounds resin per ton fiber) based on the total weight of the composite.

In another aspect, the present invention provides methods for producing a reticulated absorbent composite. The reticulated absorbent composite of the present invention can be formed by wet-laid and foam processes known to those of ordinary skill in the pulp processing art. A representative example of a wet-laid process is described in U.S. Pat. No. 5,300,192, issued Apr. 5, 1994, entitled "Wet-laid Fiber Sheet Manufacturing with Reactivatable Binders for Binding Particles to Fibers", expressly incorporated herein by reference. Wet-laid processes are also described in standard texts, such as Casey, PULP AND PAPER, 2nd edition, 1960, Volume II, Chapter VIII—Sheet Formation. Representative foam processes useful in forming the composite of the present invention are known in the art and include those described in U.S. Pat. Nos. 3,716,449; 3,839,142; 3,871,952; 3,937,273; 3,938,782; 3,947,315; 4,166,090; 4,257,754; and 5,215,627, assigned to Wiggins Teape and related to the formation of fibrous materials from foamed aqueous fiber suspensions, and "The Use of an Aqueous Foam as a Fiber-Suspending Medium in Quality Papermaking," Foams, Proceedings of a Symposium organized by the Society of Chemical Industry, Colloid and Surface Chemistry Group, R. J. Akers, Ed., Academic Press, 1976, which describes the Radfoam process, all expressly incorporated herein by reference.

In the methods of the present invention, the absorbent material is incorporated into the composite during the formation of the composite. Generally, the methods for forming the reticulated absorbent composite include combining the components of the composite in a dispersion medium (e.g., an aqueous medium) to form a slurry and then depositing the slurry onto a foraminous support (e.g., a forming wire) and dewatering to form a wet composite. Drying the wet composite provides the reticulated composite.

As noted above, the reticulated composite of the present invention is prepared from a combination of fibers, absorbent material, and optionally a wet strength agent in a dispersion medium. In one embodiment of the method, a slurry is formed by directly combining fibers, absorbent material, and wet strength agent in a dispersion medium. In another embodiment, the slurry is prepared by first combining fibers and the wet strength agent in a dispersion medium to provide a fibrous slurry to which is then added absorbent material in a second step. In yet another embodiment, a fibrous slurry is combined with a second slurry containing absorbent material, the combined slurry then being deposited onto the support. Alternatively, individual slurries, for example, a fibrous slurry and a slurry containing absorbent material, can be deposited onto the foraminous support through the use of a divided headbox, for example, a twin slice headbox that deposits two slurries onto a support simultaneously.

In one embodiment, the slurry or slurries containing the composite's components in a dispersion medium are deposited onto a foraminous support. Once deposited onto the support, the dispersion medium begins to drain from the deposited fibrous slurry. Removal of the dispersion medium (e.g., dewatering) from the deposited fibrous slurry continues through, for example, the application of heat, pressure, vacuum, and combinations thereof, and results in the formation of a wet composite.

The reticulated absorbent composite of the present invention is ultimately produced by drying the wet composite. Drying removes the remaining dispersion medium and provides an absorbent composite having the desired moisture content. Generally, the composite has a moisture content less than about 20 percent and preferably has a moisture content in the range from about 6 to about 10 percent by weight based on the total weight of the composite. Suitable composite drying methods include, for example, the use of drying cans, air floats and through air dryers. Other drying methods and apparatus known in the pulp and paper industry may also be used. Drying temperatures, pressures, and times are typical for the equipment and methods used, and are known to those of ordinary skill in the art in the pulp and paper industry. A representative wet-laid method for forming a reticulated absorbent composite of the invention is described in Example 1.

For foam methods, the fibrous slurry is an aqueous or foam slurry that further includes a surfactant. Suitable surfactants include ionic, nonionic, and amphoteric surfactants known in the art. A representative foam method for forming a reticulated absorbent composite of the invention is described in Example 2.

In the methods, the weight percent of the absorbent material in the deposited slurry will be from about 5 to about 80 percent by weight; fibers will be present in the deposited slurry in an amount from about 20 to about 80 percent by weight; and the wet strength agent will be present in an amount from about 0.01 to about 2 percent by weight, based on the total weight of the absorbent material, the fiber, and the wet strength agent in the slurry. The combined weight of the absorbent material and the fiber in the slurry (i.e., the consistency of the slurry) can range from about 0.05 to about 15 percent by weight based on the total weight of the absorbent material, fiber, and dispersion medium.

The deposition of the components of the absorbent composite onto the foraminous support, followed by dewatering, results in the formation of a wet composite that includes absorbent material that may have absorbed water and, as a result, swollen in size. The wet composite containing the water-swollen absorbent material is distributed onto a support from which water (i.e., the dispersion medium) can be withdrawn and the wet composite dried. Drying causes the water-swollen absorbent material to dehydrate and decrease in size, thereby creating voids in the composite surrounding the absorbent material.

In the methods of the present invention, the absorbent material preferably absorbs less than about 20 times its weight in the dispersion medium, more preferably less than about 10 times, and even more preferably less than about 5 times its weight in the dispersion medium.

Foam methods are advantageous for forming the absorbent composite of the present invention for several reasons. Generally, foam methods provide fibrous webs that possess both relatively low density and relatively high tensile strength. For webs composed of substantially the same components, foam-formed webs generally have densities greater than air-laid webs and lower than wet-laid webs. Similarly, the tensile strength of foam-formed webs is substantially greater than for air-laid webs and approaches the strength of wet-laid webs. Also, the use of foam forming technology allows better control of pore and void size, void size to be maximized, the orientation and uniform distribution of fibers, and the incorporation of a wide range of materials (e.g., long and synthetic fibers that cannot be readily incorporated into wet-laid processes) into the composite.

For fabrication, the reticulated absorbent composite can be formed by a foam process, preferably a process by Ahlstrom Company (Helsinki, Finland). The process encompasses desirable manufacturing efficiencies while producing a product with desirable performance characteristics.

The formation of a reticulated absorbent composite of the present invention by representative wet-laid and foam processes is described in Examples 1 and 2, respectively. Absorbent properties (i.e., rewet, acquisition time, liquid distribution, dry strength, and resilience) for representative reticulated absorbent composites are described in Examples 3 and 4. Wicking and liquid distribution for a representative absorbent composite are described in Examples 5 and 6, respectively. The tensile strength of representative composites formed in accordance with the present invention is described in Example 7. The softness (i.e., Taber stiffness) of representative wet-laid and foam-formed composites is described in Example 8.

One variable that affects the absorbent composite's performance characteristics including, for example, liquid acquisition and distribution rate and absorbent capacity, is the extent of swelling of the absorbent material in the composite. The methods of the present invention allow for control and variation of absorbent material swelling. Absorbent material swelling generally depends on the degree of crosslinking (e.g., surface and internal crosslinking) and the amount of water absorbed by the absorbent material. The extent of swelling depends on a number of factors including the type of absorbent material, the concentration of absorbent material in an aqueous environment (e.g., the dispersion medium and the wet composite), and the period of time that the absorbent material remains in contact with such an environment. Generally, the lower the concentration of the absorbent material in an aqueous medium and the longer the contact time, the greater the swelling of an absorbent material. Absorbent material swelling can be minimized by dispensing the absorbent in chilled water.

In general, the greater the initial swelling of the absorbent material, the greater the void volume and, consequently, the lower the density of the resulting absorbent composite. The greater the void volume of a composite, the greater its liquid acquisition rate and, generally, the greater the composite's absorbent capacity.

As noted above, the composite's voids are formed by the hydration and swelling of absorbent material (i.e., during wet composite formation) and the subsequent dehydration and decrease in size of the absorbent material (i.e., during wet composite drying). Ultimately, the density of the composite depends on the extent to which the absorbent material absorbs liquid and swells during the formation of the wet composite, and the conditions and extent to which the wet composite incorporating the swollen absorbent material is dried. Water absorbed by the absorbent material during wet composite formation is removed from the absorbent material, decreasing its size, on drying the wet composite. The dehydration of the swollen absorbent material defines some of the voids in the fibrous composite.

Figure 10:
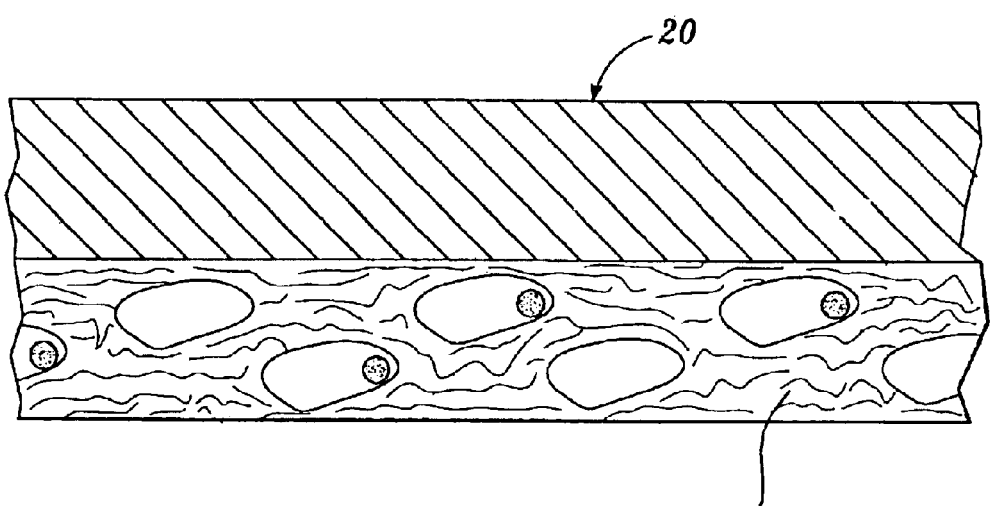
FIG. 10 is a cross-sectional view of a portion of an absorbent construct incorporating a reticulated absorbent composite formed in accordance with the present invention.
Figure 11:
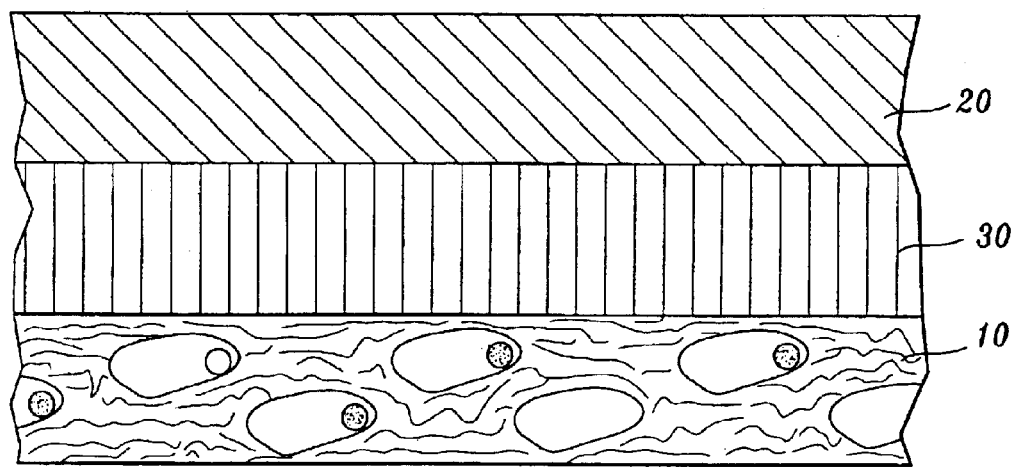
FIG. 11 is a cross-sectional view of a portion of another absorbent construct incorporating a reticulated absorbent composite formed in accordance with the present invention.

The reticulated absorbent composite of the present invention can be incorporated as an absorbent core or storage layer in an absorbent article including, for example, a diaper or feminine care product. The absorbent composite can be used alone or, as illustrated in FIGS. 10 and 11, can be used in combination with one or more other layers. In FIG. 10, absorbent composite 10 is employed as a storage layer in combination with upper acquisition layer 20. As illustrated in FIG. 11, a third layer 30 (e.g., distribution layer) can also be employed, if desired, with absorbent composite 10 and acquisition layer 20.

A variety of suitable absorbent articles can be produced from the absorbent composite. The most common include absorptive consumer products, such as diapers, feminine hygiene products such as feminine napkins, and adult incontinence products. For example, referring to FIG. 12, absorbent article 40 comprises absorbent composite 10 and overlying acquisition layer 20. A liquid pervious facing sheet 22 overlies acquisition composite 20, and a liquid impervious backing sheet 24 underlies absorbent composite 10. The absorbent composite will provide advantageous liquid absorption performance for use in, for example, diapers. The reticulated structure of the absorbent composite will aid in fluid transport and absorption in multiple wettings. For absorbent articles that incorporate the composite of the invention and that are suitable for use as diapers or as incontinence products, the articles can further include leg gathers.

Figure 12:
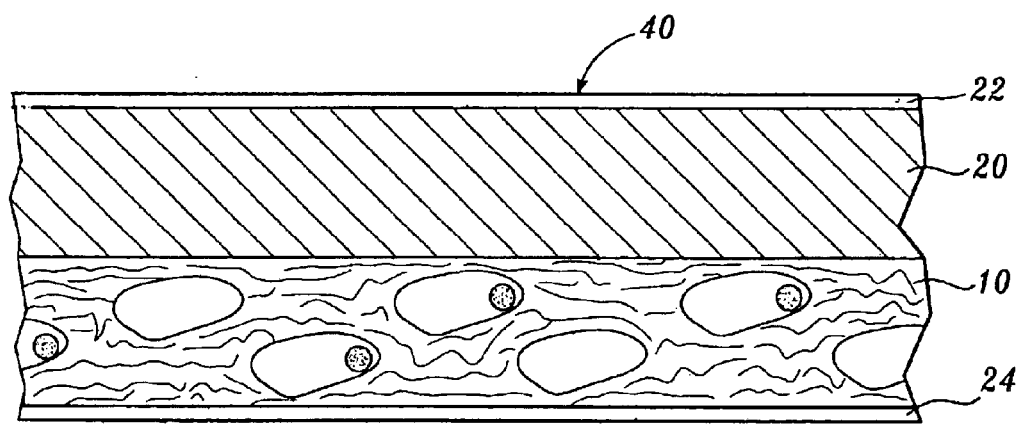
FIG. 12 is a cross-sectional view of a portion of an absorbent article incorporating a reticulated absorbent composite formed in accordance with the present invention.
Figure 13:
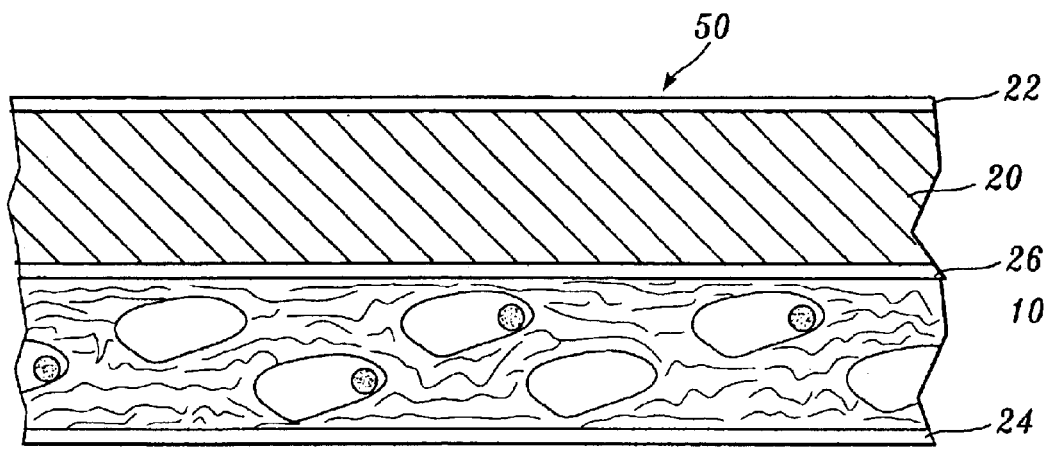
FIG. 13 is a cross-sectional view of a portion of another absorbent article incorporating a reticulated absorbent composite formed in accordance with the present invention.

The construct in FIG. 12 is shown for purposes of exemplifying a typical absorbent article, such as a diaper or feminine napkin. One of ordinary skill will be able to make a variety of different constructs using the concepts taught herein. For example, a typical construction of an adult incontinence absorbent structure is shown in FIG. 13. The article 50 comprises a facing sheet 22, acquisition layer 20, absorbent composite 10, and a backing sheet 24. The facing sheet 22 is pervious to liquid while the backing sheet 24 is impervious to liquid. In this construct, a liquid pervious tissue 26 composed of a polar, fibrous material is positioned between absorbent composite 10 and acquisition layer 20.

Figure 14:
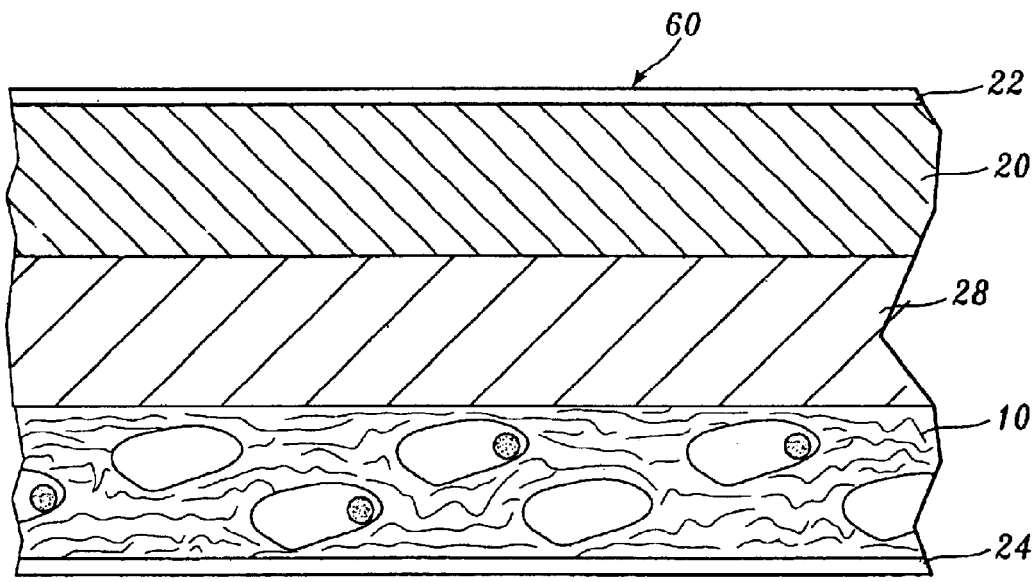
FIG. 14 is a cross-sectional view of a portion of another absorbent article incorporating a reticulated absorbent composite formed in accordance with the present invention.

Referring to FIG. 14, another absorbent article includes a facing sheet 22, an acquisition layer 20, an intermediate layer 28, absorbent composite 10, and a backing sheet 24. The intermediate layer 28 contains, for example, a densified fibrous material such as a combination of cellulose acetate and triacetin, which are combined prior to forming the article. The intermediate layer 28 can thus bond to both absorbent composite 10 and acquisition layer 20 to form an absorbent article having significantly more integrity than one in which the absorbent composite and acquisition layer are not bonded to each other. The hydrophilicity of layer 28 can be adjusted in such a way as to create a hydrophilicity gradient among layers 10, 28, and 20.

Figure 15:
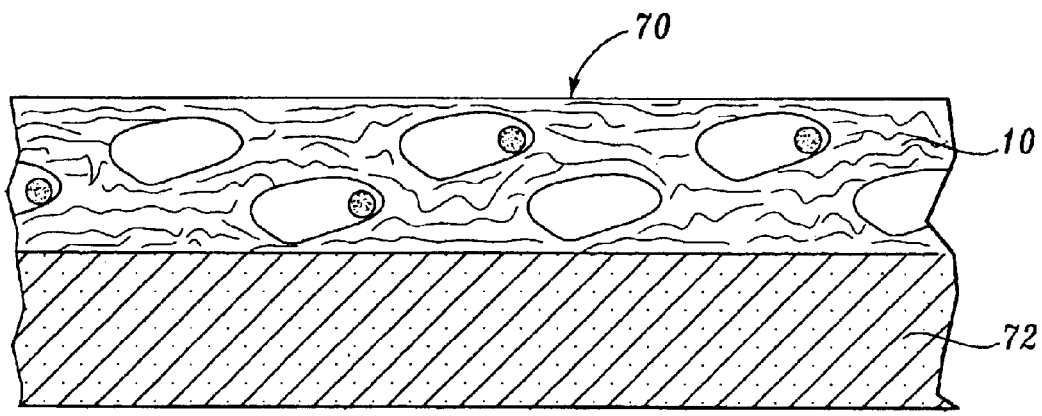
FIG. 15 is a cross-sectional view of a portion of an absorbent construct incorporating a reticulated absorbent composite formed in accordance with the present invention.

The reticulated absorbent composite of the present invention can also be incorporated as a liquid management layer in an absorbent article such as a diaper. In such an article, the composite can be used in combination with a storage core or layer. In the combination, the liquid management layer can have a top surface area that is smaller, the same size, or greater than the top surface area of the storage layer. Representative absorbent constructs that incorporate the reticulated absorbent composite in combination with a storage layer are shown in FIG. 15. Referring to FIG. 15, absorbent construct 70 includes reticulated composite 10 and storage layer 72. Storage layer 72 is preferably a fibrous layer that includes absorbent material. The storage layer can be formed by any method including air-laid, wet-laid, and foam-forming methods. The storage layer can be a reticulated composite of this invention.

Figure 16:
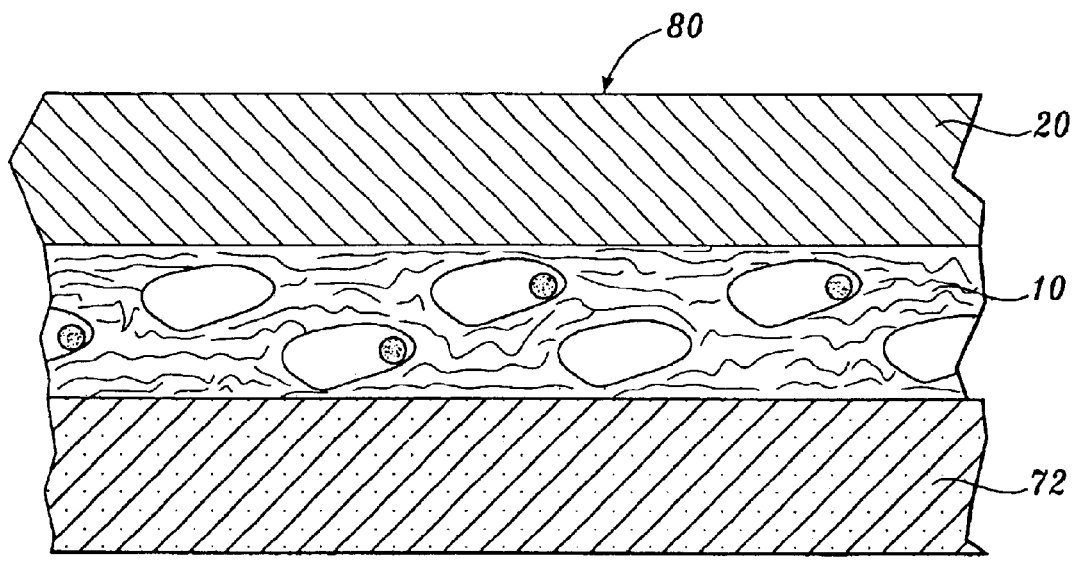
FIG. 16 is a cross-sectional view of a portion of another absorbent construct incorporating a reticulated absorbent composite formed in accordance with the present invention.
Figure 17:
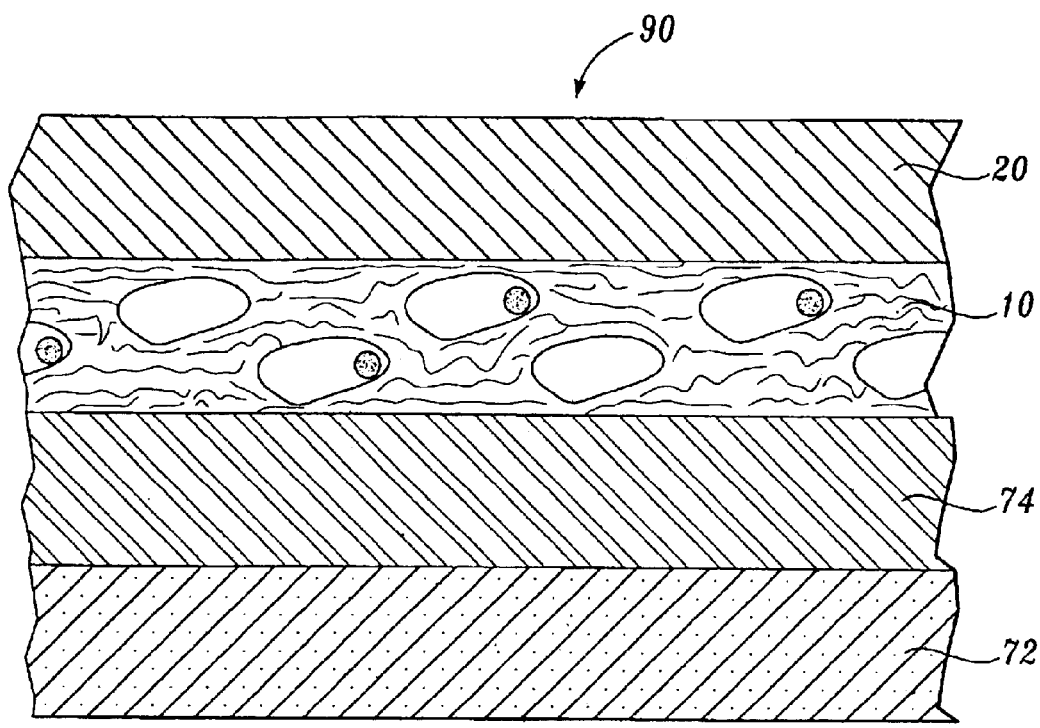
FIG. 17 is a cross-sectional view of a portion of another absorbent construct incorporating a reticulated absorbent composite formed in accordance with the present invention.

An acquisition layer can be combined with the reticulated composite and storage layer. FIG. 16 illustrates absorbent construct 80 having acquisition layer 20 overlying composite 10 and storage layer 72. Construct 80 can further include intermediate layer 74 to provide construct 90 shown in FIG. 17. Intermediate layer 74 can be, for example, a tissue layer, a nonwoven layer, an air-laid or wet-laid pad, or a reticulated composite of the invention.

Figure 18:
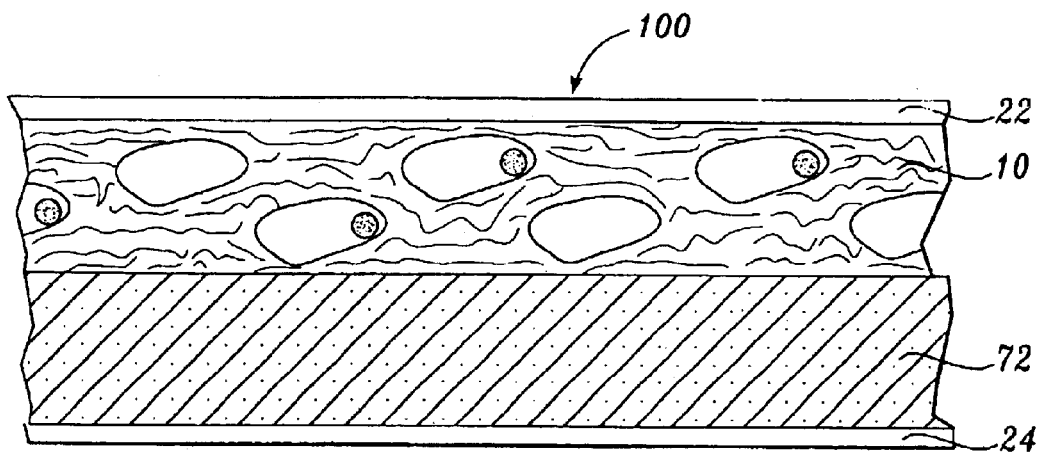
FIG. 18 is a cross-sectional view of a portion of an absorbent article incorporating a reticulated absorbent composite formed in accordance with the present invention.
Figure 19:
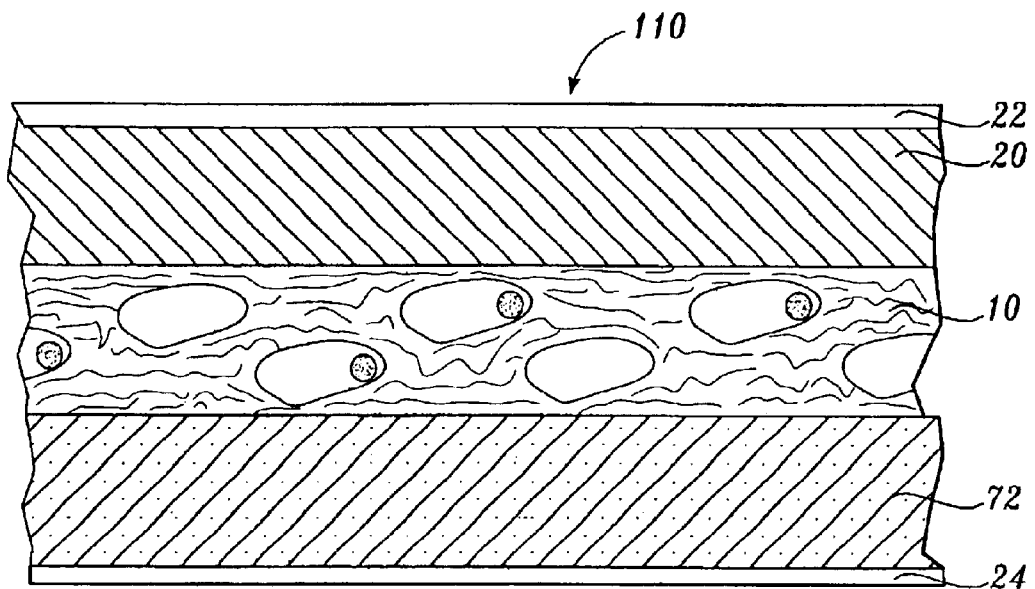
FIG. 19 is a cross-sectional view of a portion of another absorbent article incorporating a reticulated absorbent composite formed in accordance with the present invention.
Figure 20:
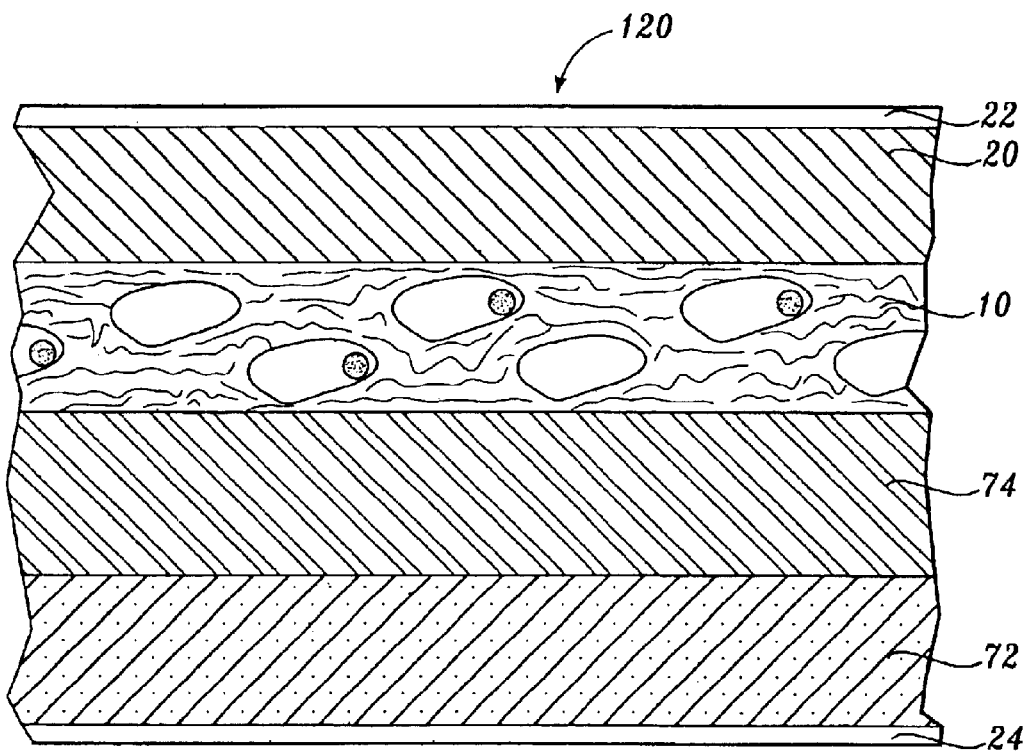
FIG. 20 is a cross-sectional view of a portion of another absorbent article incorporating a reticulated absorbent composite formed in accordance with the present invention.

Constructs 70, 80, and 90 can be incorporated into absorbent articles. Generally, absorbent articles 100, 110, and 120, shown in FIGS. 18–20, respectively, include a liquid pervious facing sheet 22, a liquid impervious backing sheet 24, and constructs 70, 80, and 90, respectively. In such absorbent articles, the facing sheet is joined to the backing sheet.

The following examples are provided for the purposes of illustration, and not limitation.

EXAMPLES

Example 1

Reticulated Absorbent Composite Formation: Representative Wet-laid Method

This example illustrates a wet-laid method for forming a representative absorbent composite of the present invention.

A wet-laid composite formed in accordance with the present invention is prepared utilizing standard wet-laid apparatus known to those in the art. A slurry of a mixture of standard wood pulp fibers and crosslinked pulp fibers (48 and 12 percent by weight, respectively, based on total weight of dried composite) in water having a consistency of about 0.25 to 3 percent is formed. Consistency is defined as the weight percent of fibers present in the slurry, based on the total weight of the slurry. A wet strength agent such as Kymene® (0.5 percent based on total composite weight) is then added to the fibrous mixture. Finally, absorbent material (40 percent by weight based on total weight of dried composite) is added to the slurry, the slurry is thoroughly mixed, and then distributed onto a wire mesh to form a wet composite. The wet composite is dried to a moisture content of about 9 to about 15 weight percent based on total composite weight to form a representative reticulated absorbent composite.

Absorbent composites having a variety of basis weights can be prepared from the composite formed as described above by pre- or postdrying densification methods known to those in the art.

Example 2

Reticulated Absorbent Composite Formation: Representative Foam Method

This example illustrates a foam method for forming a representative absorbent composite of the present invention.

A lab-size Waring blender is filled with 4L of water and pulp fibers are added. The mixture is blended for a short time. Crosslinked cellulose fibers are then added to the pulp fibers and blended for at least one minute to open the crosslinked fibers and effect mixing of the two fibers. The resulting mixture may contain from 0.07 to 12 percent by weight of solids.

The mixture is placed in a container and blended for a few seconds with an air-entrapping blade. A surfactant (Incronan 30, Croda, Inc.) is added to the blended mixture. Approximately 1 g active surfactant solids per gram of fiber is added. The mixture is blended while slowly raising the mixer blade height from the rising foam. After about one minute, the mixing is terminated, superabsorbent is added, and the mixing is restarted for another one-half minute at constant mixer blade height. The resulting foam-fiber mixture will have a volume about three times the volume of the original mixture.

The mixture is rapidly poured into a sheet mold having an inclined diffusion plate. After the addition of the mixture, the plate is removed from the mold, and a strong vacuum is applied to reduce the foam-fiber height. After most of the visible foam disappears, the vacuum is discontinued and the resulting sheet removed from the mold and passed, along with a forming wire, over a slit couch to remove excess foam and water.

The sheet is then dried in a drying oven to remove the moisture.

Example 3

Acquisition Times for a Representative Reticulated Absorbent Composite

In this example, the acquisition time for a representative reticulated absorbent composite of the present invention (Composite A) is compared to a commercially available diaper (Diaper A, Kimberly-Clark).

The tests were conducted on commercially available diapers (Kimberly-Clark) from which the core and surge management layer were removed and the surrounds used. The test diapers were prepared by inserting the absorbent composite into the diaper.

The aqueous solution used in the tests is a synthetic urine available from National Scientific under the trade name RICCA. The synthetic urine is a saline solution containing 135 meq./L sodium, 8.6 meq./L calcium, 7.7 meq./L magnesium, 1.94% urea by weight (based on total weight), plus other ingredients.

A sample of the absorbent structure was prepared for the test by determining the center of the structure's core, measuring 1 inch to the front for liquid application location, and marking the location with an "X". Once the sample was prepared, the test was conducted by first placing the sample on a plastic base (4¾ inch×19¼ inch) and then placing a funnel acquisition plate (4 inch×4 inch plastic plate) on top of the sample with the plate's hole positioned over the "X". A donut weight (1400 g) was then placed on top of the funnel acquisition plate to which was then attached a funnel (4-inch diameter). Liquid acquisition was then determined by pouring 100 mL synthetic urine into the funnel and measuring the time from when liquid was first introduced into the funnel to the time that liquid disappeared from the bottom of the funnel into the sample. The measured time is the acquisition time for the first liquid insult. After waiting one minute, a second 100 mL portion was added to the funnel and the acquisition time for the second insult was measured. After waiting an additional one minute, the acquisition was repeated for a third time to provide an acquisition time for the third insult. The acquisition times reported in seconds for each of the three successive 100 mL liquid insults for Diaper A and Composite A are summarized in Table 1.

TABLE 1

Acquisition Time Comparison

| | Acquisition Time (sec) | |
|---|---|---|
| Insult | Diaper A | Composite A |
| 1 | 45 | 10 |
| 2 | 60 | 11 |
| 3 | 75 | 10 |

As shown in Table 1, liquid is more rapidly acquired by the absorbent composite of the invention than for the commercially available diaper containing an air-laid storage core. The results show that the air-laid core does not acquire liquid nearly as rapidly as the composite of the invention. The commercial diaper also exhibited characteristic diminution of acquisition rate on successive liquid insults. In contrast, the composite of the invention maintained a relatively constant acquisition time as the composite continued to absorb liquid on successive insult. Significantly, the absorbent composite of the invention exhibits an acquisition time for the third insult that is substantially less (about fourfold) than that of the commercially available diaper for initial insult. The results reflect the greater wicking ability and capillary network for the wet-laid composite compared to conventional air-laid storage core in general, and the enhanced performance of the reticulated absorbent composite in particular.

Example 4

Acquisition Rate and Rewet for Representative Reticulated Absorbent Composites

In this example, the acquisition time and rewet of representative reticulated absorbent composites of the present invention (designated Composites A1–A4) are compared to a commercially available diaper (Diaper A, Kimberly-Clark). Composites A1–A4 differ by the method by which the composites were dried.

Certain properties of the tested composites including the amount of superabsorbent material (weight percent SAP) in the composite and basis weight for each of the composites are summarized in Table 2.

The tests were conducted on commercially available diapers (Kimberly-Clark) from which the cores were removed and used as surrounds. The test diapers were prepared by inserting the tested composites into the diapers.

The acquisition time and rewet are determined in accordance with the multiple-dose rewet test described below.

Briefly, the multiple-dose rewet test measures the amount of synthetic urine released from an absorbent structure after each of three liquid applications, and the time required for each of the three liquid doses to wick into the product.

The aqueous solution used in the tests was a synthetic urine available from National Scientific under the trade name RICCA, and as described above in Example 1.

A preweighed sample of the absorbent structure was prepared for the test by determining the center of the structure's core, measuring 1 inch to the front for liquid application location, and marking the location with an "X". A liquid application funnel (minimum 100 mL capacity, 5–7 mL/s flow rate) was placed 4 inches above the surface of the sample at the "X". Once the sample was prepared, the test was conducted as follows. The sample was flattened, nonwoven side up, onto a tabletop under the liquid application funnel. The funnel was filled with a dose (100 mL) of synthetic urine. A dosing ring (5/32 inch stainless steel, 2 inch ID×3 inch height) was placed onto the "X" marked on the samples. A first dose of synthetic urine was applied within the dosing ring. Using a stopwatch, the liquid acquisition time was recorded in seconds from the time the funnel valve was opened until the liquid wicked into the product from the bottom of the dosing ring. After a twenty-minute wait period, rewet was determined. During the twenty minute wait period after the first dose was applied, a stack of filter papers (19–22 g, Whatman #3, 11.0 cm or equivalent, that had been exposed to room humidity for minimum of 2 hours before testing) was weighed. The stack of preweighed filter papers was placed on the center of the wetted area. A cylindrical weight (8.9 cm diameter, 9.8 lb.) was placed on top of these filter papers. After two minutes the weight was removed, the filter papers were weighed and the weight change recorded. The procedure was repeated two more times. A second dose of synthetic urine was added to the diaper, and the acquisition time was determined; filter papers were placed on the sample for two minutes, and the weight change determined. For the second dose, the weight of the dry filter papers was 29–32 g, and for the third dose, the weight of the filter papers was 39–42 g. The dry papers from the prior dosage were supplemented with additional dry filter papers.

Liquid acquisition time is reported as the length of time (seconds) necessary for the liquid to be absorbed into the product for each of the three doses. The results are summarized in Table 2.

Rewet is reported as the amount of liquid (grams) absorbed back into the filter papers after each liquid dose (i.e., difference between the weight of wet filter papers and the weight of dry filter papers). The results are also summarized in Table 2.

TABLE 2

Acquisition Time and Rewet Comparison

| Composite | SAP % (w/w) | Basis Weight (gsm) | Acquisition Time (sec) | | | Rewet (g) | | |
|---|---|---|---|---|---|---|---|---|
| | | | Insult 1 | Insult 2 | Insult 3 | Insult 1 | Insult 2 | Insult 3 |
| A1 | 49.4 | 568 | 16 | 19 | 26 | 0.1 | 0.4 | 2.4 |
| A2 | 38.3 | 648 | 17 | 19 | 22 | 0.1 | 0.7 | 2.5 |
| A3 | 35.9 | 687 | 29 | 26 | 27 | 0.2 | 0.2 | 0.7 |
| A4 | 38.8 | 672 | 17 | 18 | 21 | 0.1 | 0.3 | 0.9 |
| Commercial air-laid core | 40.0 | 625 | 34 | 35 | 39 | 0.1 | 4.0 | 12.6 |

As indicated in Table 2, the acquisition times for representative composites of the invention (Composites A1–A4) were significantly less than for the commercially available core.

The rewet of the representative composites of the invention (Composites A1–A4) is significantly less than for the other cores. While the composites exhibited relatively low rewet initially, after the third insult the commercially available core showed substantial rewet. In contrast, Composites A continued to exhibit low rewet.

Example 5

Horizontal and Vertical Wicking for a Representative Reticulated

Absorbent Composite

In this example, the wicking characteristics of a representative reticulated absorbent composite (Composite A) are compared to a commercially available diaper storage core (Diaper B, Procter & Gamble).

The horizontal wicking test measures the time required for liquid to horizontally wick preselected distances. The test was performed by placing a sample composite on a horizontal surface with one end in contact with a liquid bath and measuring the time required for liquid to wick preselected distances. Briefly, a sample composite strip (40 cm×10 cm) was cut from a pulp sheet or other source. If the sheet has a machine direction, the cut was made such that the 40 cm length of the strip was parallel to the machine direction. Starting at one end of the 10 cm width of the strip, a first line was marked at 4.5 cm from the strip edge and then consecutive lines at 5 cm intervals were marked along the entire length of the strip (i.e., 0 cm, 5 cm, 10 cm, 15 cm, 20 cm, 25 cm, 30 cm, and 35 cm). A horizontal wicking apparatus having a center trough with level horizontal wings extending away from opposing sides of the trough was prepared. The nonsupported edge of each wing was positioned to be flush with the inside edge of the trough. On each wing's end was placed a plastic extension to support each wing in a level and horizontal position. The trough was then filled with synthetic urine. The sample composite strip was then gently bent at the 4.5 cm mark to form an approximately 45° angle in the strip. The strip was then placed on the wing such that the strip lay horizontally and the bent end of the strip extended into and contacted the liquid in the trough. Liquid wicking was timed beginning from when the liquid reached the first line marked on the composite 5 cm from the 4.5 cm bend. The wicking time was then recorded at 5 cm intervals when 50 percent of the liquid front reached the marked interval (e.g., 5 cm, 10 cm). The liquid level in the trough was maintained at a relatively constant level throughout the test by replenishing with additional synthetic urine. The horizontal wicking results are summarized in Table 3.

TABLE 3

Horizontal Wicking Comparison

| Distance (cm) | Wicking Time (sec) | |
|---|---|---|
| | Diaper B | Composite A |
| 5 | 48 | 15 |
| 10 | 150 | 52 |
| 15 | 290 | 134 |
| 20 | 458 | 285 |
| 25 | 783 | 540 |
| 30 | 1703 | 1117 |
| 35 | — | 1425 |

The results tabulated above indicate that horizontal wicking is enhanced for absorbent composite of the invention compared to a conventional air-laid core. The wicking time for Composite A is about 50 percent of that for the conventional diaper core. Thus, the horizontal wicking for Composite A is about 1.5 to about 3 times that of a commercially available storage core.

The vertical wicking test measures the time required for liquid to vertically wick preselected distances. The test was performed by vertically suspending a sample composite with one end of the composite in contact with a liquid bath and measuring the time required for liquid to wick preselected distances. Prior to the test, sample composites (10 cm×22 cm) were cut and marked with consecutive lines 1 cm, 11 cm, 16 cm, and 21 cm from one of the strip's edges. Preferably, samples were preconditioned for 12 hours at 50 percent relative humidity and 23° C. and then stored in sample bags until testing. The sample composite was oriented lengthwise vertically and clamped from its top edge at the 1 cm mark allowing its bottom edge to contact a bath containing synthetic urine. Timing was commenced once the strip was contacted with the liquid. The time required for 5 percent of the wicking front to reach 5 cm, 10 cm, 15 cm, and 20 cm was then recorded. The vertical wicking results are summarized in Table 4.

TABLE 4

Vertical Wicking Comparison

| Distance (cm) | Wicking Time (sec) | |
|---|---|---|
| | Diaper B | Composite A |
| 5 | 20 | 6 |
| 10 | Fell Apart | 54 |
| 15 | — | 513 |
| 20 | — | 3780 |

As for the horizontal wicking results, Composite A had significantly greater vertical wicking compared to the commercial core. The results also show that the composite of the invention has significantly greater wet tensile strength compared to the conventional air-laid composite.

Example 6

Liquid Distribution for a Representative Reticulated Absorbent Composite

In this example, the distribution of liquid in a reticulated absorbent composite (Composite A) is compared to that of two commercially available diapers (Diapers A and B above). The test measures the capacity of a diaper core to distribute acquired liquid. Perfect distribution would have 0% deviation from average. Ideal liquid distribution would result in equal distribution of the applied liquid in each of the four distribution zones (i.e., about 25% liquid in each zone).

Liquid distribution is determined by weighing different zones of a sample that has been subjected to the multiple-dose rewet test described above in Example 4. Basically, after the last rewet, the wings of the diaper are removed and then cut into four equal length distribution zones. Each zone is then weighed to determine the weight of liquid contained in each zone.

The liquid distribution results for a representative reticulated absorbent composite of the invention approaches ideality. The results indicate that, while the representative commercial storage cores accumulate liquid near the site of insult, liquid is efficiently and effectively distributed throughout the reticulated absorbent storage core.

Example 7

Wet and Dry Tensile Strength for a Reticulated Absorbent Composite

In this example, the measurement of wet and dry tensile strength of a representative absorbent composite is described.

A dry pad tensile integrity test is performed on a 4 inch by 4 inch square test pad by clamping a dry test pad along two opposing sides. About 3 inches of pad length are left visible between the clamps. The sample is pulled vertically in an Instron testing machine and the tensile strength measured is reported in N/m. The tensile strength is converted to tensile index, Nm/g, by dividing the tensile strength by the basis weight g/m$^2$.

A wet tensile integrity test is performed by taking a sample composite from that which has been immersed in synthetic urine for 10 minutes and then allowed to drain for 5 minutes and placing the sample in a horizontal jug. Opposite ends of the sample are clamped and then pulled horizontally on the Instron testing machine. The wet tensile strength, N/m, is converted to tensile index, Nm/g, by dividing the tensile strength by the basis weight g/m$^2$.

Typically, increasing the amount of Kymene® from 2 to 100 pounds per ton of fiber may increase the dry tensile strength from about 0.15 Nm/g to 0.66 Nm/g and the wet tensile strength from about 1.5 Nm/g to about 2.4 Nm/g.

Example 8

Taber Stiffness for Representative Reticulated Absorbent Composites

The stiffness of representative reticulated absorbent composites formed in accordance with the present invention was determined by the Taber stiffness method. Representative composites were formed by wet-laid and foam methods. These composites included matrix fibers (48 percent by weight, southern pine commercially available from Weyerhaeuser Co. under the designation NB416), resilient fibers (12 percent by weight, polymaleic acid crosslinked fibers), and absorbent material (40 percent by weight, superabsorbent material commercially available from Stockhausen). One of the wet-laid and one of the foam-formed composites further included a wet strength agent (about 0.5 percent by weight, polyamide-epichlorohydrin resin commercially available from Hercules under the designation Kymene®).

The stiffness of the foam-formed composites was significantly lower than the similarly constituted wet-laid composites. The results also indicate that, for the wet-laid composites, the inclusion of a wet strength agent increases the composites' stiffness.

While the preferred embodiment of the invention has been illustrated and described, it will be appreciated that various changes can be made therein without departing from the spirit and scope of this invention.

The embodiments of the invention in which an exclusive property or privilege is claimed are defined as follows:

1. A method for forming an absorbent composite, comprising the steps of:
    adding superabsorbent particles to a first fibrous slurry comprising crosslinked cellulosic fibers in a dispersion medium to form a second fibrous slurry;
    depositing the second fibrous slurry on a foraminous support to form a wet composite; and
    drying the wet composite to form an absorbent composite comprising a fibrous matrix and superabsorbent particles,
    wherein the fibrous matrix defines voids and passages between voids distributed substantially throughout the matrix;
    wherein superabsorbent particles are located within some of the voids; and
    wherein superabsorbent particles located within the voids are expandable into the voids.

2. The method of claim 1 wherein the first fibrous slurry further comprises wood pulp fibers.

3. The method of claim 1 wherein the superabsorbent particles are swellable in the dispersion medium.

4. The method of claim 1 wherein the superabsorbent particles absorb less than about 20 times its weight in the dispersion medium.

5. The method of claim 1 wherein the first fibrous slurry further comprises a wet strength agent.

6. The method of claim 5 wherein the wet strength agent is a polyamide-epichlorohydrin resin.

7. The method of claim 1 wherein the dispersion medium comprises water.

8. The method of claim 1 wherein the dispersion medium further comprises a surfactant.

9. The method of claim 8 wherein the surfactant is selected from the group consisting of ionic, nonionic, and amphoteric surfactants.

10. The method of claim 1 wherein the second fibrous slurry has a consistency of from about 0.05 to about 15 percent solids by weight.

11. The method of claim 1 wherein the method is a wet-laid method.

12. The method of claim 1 wherein the method is a foam method.

13. The method of claim 1 wherein the adding superabsorbent particles to crosslinked cellulosic fibers comprises adding the superabsorbent particles as a chilled water suspension.

14. A method for forming an absorbent composite, comprising the steps of:
    combining superabsorbent particles with a dispersion medium to form an superabsorbent particle slurry;
    adding the superabsorbent particle slurry to a fibrous slurry comprising crosslinked cellulosic fibers to provide a fibrous superabsorbent particle slurry;
    depositing the fibrous superabsorbent particle slurry on a foraminous support to form a wet composite; and drying the wet composite to form an absorbent composite comprising a fibrous matrix and superabsorbent particles, wherein the fibrous matrix defines voids and passages between voids distributed substantially throughout the matrix;

wherein superabsorbent particles are located within some of the voids; and wherein the superabsorbent particles located within the voids are expandable into the voids.

15. The method of claim 14 wherein the first fibrous slurry further comprises a wet strength agent.

16. The method of claim 14 wherein the superabsorbent particle slurry comprises chilled water.

* * * * *